United States Patent
Xiao et al.

(10) Patent No.: US 12,169,195 B2
(45) Date of Patent: *Dec. 17, 2024

(54) BRACKET, THROMBELASTOGRAPHY DEVICE, AND SUPPORT SYSTEM

(71) Applicant: Haemonetics Corporation, Boston, MA (US)

(72) Inventors: Jian Xiao, Suzhou (CN); Bangzhong Yu, Suzhou (CN); Feng Jiang, Suzhou (CN)

(73) Assignee: Haemonetics Corporation, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/380,967

(22) Filed: Oct. 17, 2023

(65) Prior Publication Data

US 2024/0044866 A1    Feb. 8, 2024

Related U.S. Application Data

(63) Continuation of application No. 18/169,531, filed on Feb. 15, 2023, now Pat. No. 11,835,512, which is a
(Continued)

(30) Foreign Application Priority Data

Apr. 29, 2016   (CN) .......................... 201610278391.2
Apr. 29, 2016   (CN) .......................... 201620380641.9

(51) Int. Cl.
*G01N 33/49*   (2006.01)
*G01N 11/06*   (2006.01)
(Continued)

(52) U.S. Cl.
CPC ............. *G01N 33/49* (2013.01); *G01N 11/06* (2013.01); *G01N 11/16* (2013.01);
(Continued)

(58) Field of Classification Search
CPC ........ G01N 11/10; G01N 11/14; G01N 11/16; G01N 33/4905; G91B 2011/147
See application file for complete search history.

(56) References Cited

U.S. PATENT DOCUMENTS 4,328,701 A    5/1982   Mau-Tung et al.
5,201,214 A    4/1993   Sekiguchi et al.
(Continued)

FOREIGN PATENT DOCUMENTS

CN    104181311 A    12/2014
CN    203981539 U    12/2014
(Continued)

OTHER PUBLICATIONS

Extended European Search Report for European Patent Application No. 21209996.4, dated Jul. 6, 2022 (8 pages).
(Continued)

*Primary Examiner* — Herbert K Roberts
(74) *Attorney, Agent, or Firm* — Nutter McClennen & Fish LLP (57) ABSTRACT

A bracket a thrombelastography device, and a support system are disclosed. The bracket comprises: a fixed support part (101), a movable support part (102), and a connection part (103). The connection part comprises a first fixing connection member (1031) and a second fixing connection member (1032). The first fixing connection member is fixedly connected to the fixed support part; the second fixing connection member is fixedly connected to the movable support part; the first fixing connection member is connected to the second fixing connection member in point contact fashion, such that the first fixing connection member and the second fixing connection member can rotate relative to each other; the movable support part is fixedly connected to a supported object; when driven by the supported object, the movable support part rotates relative to the fixed support
(Continued)

part by means of the point contact between the first fixing connection member and the second fixing connection member. The thrombelastography device comprises a rotational shaft and a bracket. The rotational resistance to the supported object when it rotates can be reduced.

12 Claims, 6 Drawing Sheets

Related U.S. Application Data continuation of application No. 17/006,523, filed on Aug. 28, 2020, now Pat. No. 11,598,764, which is a continuation of application No. 16/096,981, filed as application No. PCT/CN2017/082783 on May 2, 2017, now Pat. No. 10,761,082.

(51) Int. Cl.
  *G01N 11/14* (2006.01)
  *G01N 11/16* (2006.01)
  *G01N 33/86* (2006.01)

(52) U.S. Cl.
  CPC ......... *G01N 33/4905* (2013.01); *G01N 33/86* (2013.01); *G01N 11/14* (2013.01); *G01N 2011/147* (2013.01)

(56) References Cited

U.S. PATENT DOCUMENTS

| | | | |
|---|---|---|---|
| 5,233,759 | A | 8/1993 | Gloor et al. |
| 5,987,970 | A | 11/1999 | Ball |
| 6,218,751 | B1 | 4/2001 | Bohlin |
| 8,375,771 | B1 | 2/2013 | Bi |
| 9,759,730 | B2 | 9/2017 | Rechner |
| 10,761,082 | B2 | 9/2020 | Xiao et al. |
| 11,598,764 | B2 | 3/2023 | Xiao et al. |
| 2010/0154520 | A1 | 6/2010 | Schubert et al. |
| 2010/0184201 | A1 | 7/2010 | Schubert et al. |
| 2012/0210774 | A1 | 8/2012 | Raffer |
| 2014/0047904 | A1 | 2/2014 | Mak |
| 2016/0091516 | A1 | 3/2016 | Gorin et al. |
| 2016/0356690 | A1 | 12/2016 | Amamiya et al. |
| 2017/0292941 | A1 | 10/2017 | Benson |
| 2019/0113499 | A1 | 4/2019 | Xiao et al. |
| 2020/0393441 | A1 | 12/2020 | Xiao et al. |
| 2023/0194501 | A1 | 6/2023 | Xiao et al. |

FOREIGN PATENT DOCUMENTS

| | | | |
|---|---|---|---|
| CN | 204065105 U | * | 12/2014 |
| CN | 104458503 A | | 3/2015 |
| CN | 105805176 A | | 7/2016 |
| CN | 205744966 U | | 11/2016 |
| EP | 1850134 A1 | | 10/2007 |
| EP | 2208996 A1 | | 7/2010 |
| GB | 2204701 A | | 11/1988 |
| JP | 2002502484 A | | 1/2002 |
| JP | 2007298511 A | | 11/2007 |
| JP | 2010043741 A | | 2/2010 |
| JP | 2012515340 A | | 7/2012 |
| JP | 2013200277 A | | 10/2013 |
| JP | 2015105948 A | | 6/2015 |
| WO | 2016046565 A2 | | 3/2016 |

OTHER PUBLICATIONS

International Preliminary Report on Patentability for International Application No. PCT/CN2017/082783, dated Oct. 30, 2018 (5 pages).
International Search Report issued for International Patent Application No. PCT/CN2017/082783, mailed Jun. 29, 2017 (6 pages).
Japanese Office Action issued for Japanese Patent Application No. 2019-507984, dated Mar. 29, 2021 (13 pages).
Partial Supplementary European Search Report issued for European Patent Application No. 17788840.1, dated Feb. 3, 2020 (12 pages). Jan. 21, 2020.

* cited by examiner

```
   ┌─807              ┌─801
   │                  │
┌──┴──────────┐   ┌───┴──────┐
│Rotational Shaft│─│ Bracket │
└────────────────┘ └─────────┘
```

FIG. 13

BRACKET, THROMBELASTOGRAPHY DEVICE, AND SUPPORT SYSTEM

CROSS REFERENCE TO RELATED APPLICATIONS

The present application is a continuation of U.S. application Ser. No. 18/169,531 filed Feb. 15, 2023, now U.S. Pat. No. 11,835,512, which is a continuation of U.S. application Ser. No. 17/006,523 filed Aug. 28, 2020, now U.S. Pat. No. 11,598,764, which is a continuation of U.S. application Ser. No. 16/096,981 filed Oct. 26, 2018, now U.S. Pat. No. 10,761,082, which is a national stage entry of International Application No. PCT/CN2017/082783 filed May 2, 2017, which claims the benefit of CN 201610278391.2 filed Apr. 29, 2016 and CN 201620380641.9 filed Apr. 29, 2016, the full disclosures of each which are incorporated by reference herein in their entirety.

TECHNICAL FIELD

The present invention relates to the technical field of measurement, and in particular, to a bracket, a thrombelastography device, and a support system.

BACKGROUND

A thrombelastography device is an apparatus which is configured to measure blood coagulation in vitro and comprises a rotational shaft that is rotatable. When blood is measured, the rotational shaft is inserted into the blood and rotates as the blood rotates. The blood coagulation data of blood is calculated according to the angular displacement of the rotational shaft.

SUMMARY

The present invention provides a bracket, a thrombelastography device, and a support system, which can reduce the rotational resistance encountered when a supported object rotates.

According to an aspect of the present invention, there is provided a bracket, which comprises: a fixed support part, a movable support part, and a connection part; wherein
   the connection part comprises a first fixing connection member and a second fixing connection member;
   the first fixing connection member is fixedly connected to the fixed support part;
   the second fixing connection member is fixedly connected to the movable support part;
   the first fixing connection member is connected to the second fixing connection member in point contact fashion, such that the first fixing connection member and the second fixing connection member can rotate relative to each other;
   the movable support part is fixedly connected to a supported object supported by the bracket; and
   when driven by the supported object, the movable support part rotates relative to the fixed support part by means of the point contact between the first fixing connection member and the second fixing connection member.

According to another aspect of the present invention, there is provided a thrombelastography device, which comprises a rotational shaft and the bracket as described above, wherein the rotational shaft which serves as the supported object is fixedly connected to the movable support part in the bracket; and
   the rotational shaft can drive, under a driving force of measured blood, the movable support part to rotate.

According to yet another aspect of the present invention, there is provided a support system, which comprises a supported object and the bracket described above, wherein
   the supported object is fixedly connected to the movable support part in the bracket, and can drive, under an external driving force, the movable support part to rotate.

Embodiments of the present invention provide a bracket, a thrombelastography device, and a support system. The fixed support part supports the movable support part and the supported object by means of the connection part, and the first fixing connection member and the second fixing connection member in the connection part are connected together in point contact fashion, such that the first fixing connection member and the second fixing connection member can rotate relative to each other. The supported object fixedly connected to the movable support part, which is stress, can drive the movable support part to rotate around the contact point between the first fixing connection member and the second fixing connection member. Since the first fixing connection member and the second fixing connection member are connected together in point contact fashion, when the movable support part rotates relative to the fixed support part, only one contact point generates a frictional force to impede the rotation of the movable support part. Therefore, compared with the prior art in which the frictional force is generated in the presence of a plurality of contact points or contact surfaces, the frictional force generated on the bracket may be reduced, and the rotational resistance encountered when the supported object rotates is reduced.

BRIEF DESCRIPTION OF THE DRAWINGS

In order to illustrate the embodiments of the present invention or the technical solutions in the prior art more clearly, the drawings used in the embodiments or the prior art description will be briefly described below. Apparently, the drawings in the following description are some embodiments of the present invention. For those of ordinary skill in the art, other drawings may also be obtained according to these drawings, without paying creative work.

DETAILED DESCRIPTION

In order to make the objective, the technical solution and the advantages of the embodiments of the present invention clearer, the technical solutions in the embodiments of the present invention are clearly and completely described below with reference to the accompanying drawings in the embodiments of the present invention. It is apparent that the described embodiments are part of the embodiments of the present invention, rather than all of the embodiments. All other embodiments obtained by those of ordinary skill in the art based on the embodiments of the present invention without paying creative work should fall within the protection scope of the present invention.

Figure 1:
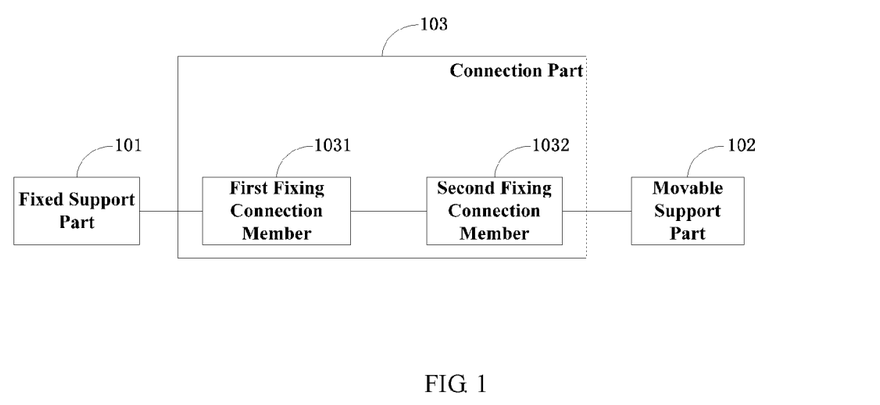
FIG. 1 is a schematic diagram of a bracket provided by an embodiment of the present invention.

As shown in FIG. 1, an embodiment of the present invention provides a bracket. The bracket comprises a fixed support part 101, a movable support part 102, and a connection part 103, wherein the connection part 3 comprises a first fixing connection member 1031 and a second fixing connection member 1032;

the first fixing connection member 1031 is fixedly connected to the fixed support part 101;

the second fixing connection member 1032 is fixedly connected to the movable support part 102;

the first fixing connection member 1031 is connected to the second fixing connection member 1032 in point contact fashion, such that the first fixing connection member and the second fixing connection member can rotate relative to each other;

the movable support part 102 is fixedly connected to a supported object; and when driven by the supported object, the movable support part 102 can rotate relative to the fixed support part 101 by means of the point contact between the first fixing connection member 1031 and the second fixing connection member 1032.

The embodiment of the present invention provides a bracket. The fixed support part supports the movable support part and the supported object by means of the connection part, and the first fixing connection member and the second fixing connection member in the connection part are connected together in point contact fashion, such that the first fixing connection member and the second fixing connection member can rotate relative to each other. The supported object fixedly connected to the movable support part, which is stress, can drive the movable support part to rotate around the contact point between the first fixing connection member and the second fixing connection member. Since the first fixing connection member and the second fixing connection member in the connection part are connected in point contact fashion, when the movable support part rotates relative to the fixed support part, only one contact point generates a frictional force to impede the rotation of the movable support part. Therefore, compared with the prior art in which the frictional force is generated in the presence of a plurality of contact points or contact surfaces, the frictional force generated on the bracket may be reduced, and the rotational resistance encountered when the supported object rotates is reduced.

In an embodiment provided by the present invention, the point connection may be in a manner that two contact components are not in full contact and the contact area is less than a predetermined value. For example, when the first fixing connection member and the second fixing connection member are connected together in point contact fashion, the contact area is less than 1 square millimeter.

In an embodiment of the present invention, the first fixing connection member is a bearing and the second fixing connection member is of a tapered structure; or the first fixing connection member is of a tapered structure, and the second fixing connection member is a bearing, wherein the bearing is provided with a tapered groove, and the tip of the tapered structure is located in the tapered groove and is in contact with the bottom of the tapered groove, such that the tapered structure is connected to the bearing in point contact fashion, and therefore the first fixing connection member and the second fixing connection member can rotate relative to each other. The bearing is made of any material that is appropriately rigid to reduce the frictional force with the tapered structure, such as gemstones, glass, alloys, metals, or the like. The size and shape of the bearing are any suitable size and shape that facilitate connection with the movable support part or fixed support part and facilitate the provision of the tapered groove that is matched with the tapered structure. For example, the bearing has a cylindrical shape with a tapered groove on the upper surface, and the diameter of the cylindrical shape and the diameter of the tapered groove are appropriately larger than the diameter of the bottom of the tapered structure.

Figure 2:
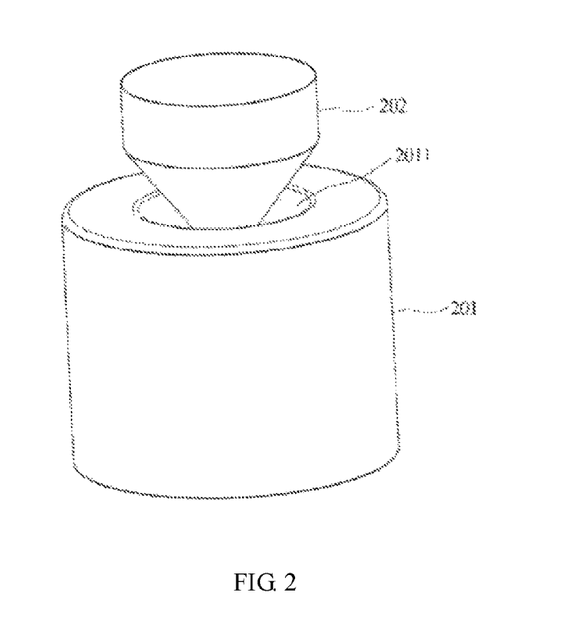
FIG. 2 is a schematic diagram of a connection part provided by an embodiment of the present invention.

In a further embodiment of the present invention, the first fixing connection member and the second fixing connection member in the connection part may be a jewel bearing and a top cone. In an example, the first fixing connection member is the jewel bearing, and the second fixing connection member is the top cone. In another example, the first fixing connection member is the top cone, and the second fixing connection member is the jewel bearing. As shown in FIG. 2, the jewel bearing 201 is of a cake structure. A tapered groove 2011 is formed in a plane of the jewel bearing 201. The top cone 202 may be of a tapered structure. The tip of the top cone 202 is located in the groove 2011, and only the tip of the top cone 202 is in contact with the bottom of the groove 2011, such that the jewel bearing 201 is connected to the top cone 202 in point contact fashion. For example, when the tip of the top cone 202 has an area of 0.8 square millimeter, the top cone is in point contact with the tapered groove 2011 of the jewel bearing 201 by means of this tip having the area of 0.8 square millimeter.

In an embodiment of the present invention, the first fixing connection member in the connection part may be a jewel bearing or a top cone. When the first fixing connection member is the jewel bearing, the second fixing connection member is a top cone. When the first fixing connection member is the top cone, the second fixing connection member is the jewel bearing. The structure of the bracket will be described below in the following cases in which the first fixing connection member is the jewel bearing and the first fixing connection member is the top cone, respectively.

Figure 3:
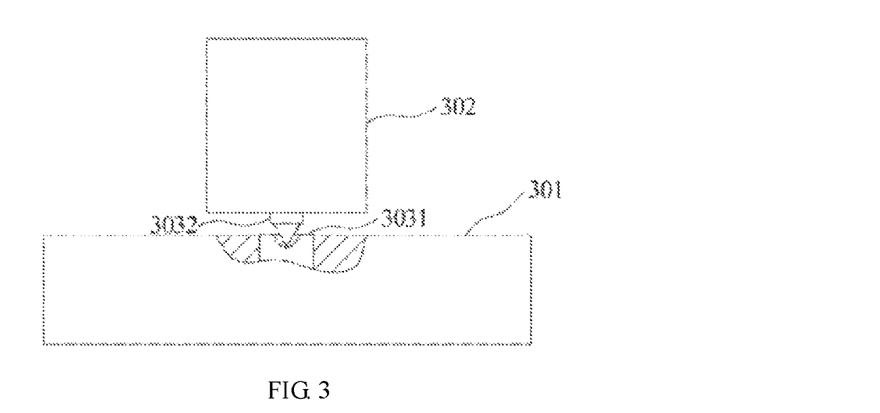
FIG. 3 is a schematic diagram of a bracket in which a jewel bearing is fixedly connected to the fixed support part as provided by an embodiment of the present invention.

In an embodiment of the present invention, as shown in FIG. 3, the jewel bearing 3031 which serves as the first fixing connection member is fixedly connected to the fixed support part 301, the top cone 3032 which serves as the second fixing connection member is fixedly connected to the movable support part 302, and the tip of the top cone 3032 is located in a groove of the jewel bearing 3031 and is in point contact with the bottom of the groove in the jewel bearing 3031. The fixed support part 301 supports, by means of the jewel bearing 3031, the top cone 3032 and the movable support part 301 which are fixedly connected.

Figure 4:
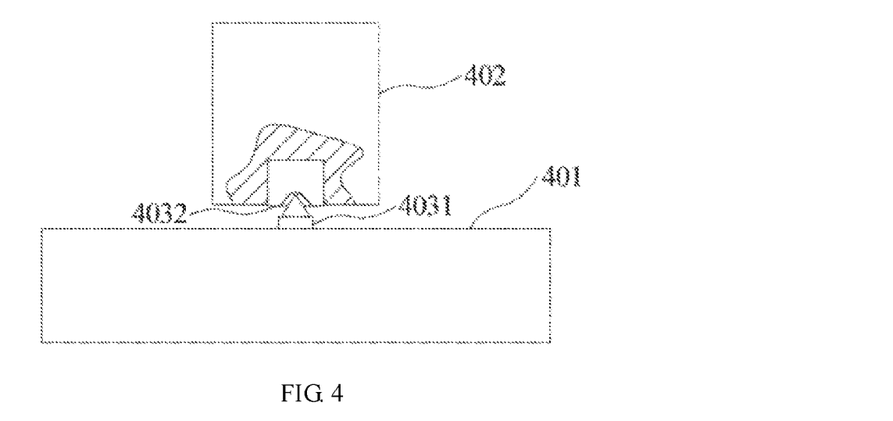
FIG. 4 is a schematic diagram of a bracket in which a jewel bearing is fixedly connected to a movable support part as provided by an embodiment of the present invention.

In an embodiment of the present invention, as shown in FIG. 4, the top cone 4031 which serves as the first fixing connection member is fixedly connected to the fixed support part 401, the jewel bearing 4032 which serves as the second fixing connection member is fixedly connected to the movable support part 402, and the tip of the top cone 4031 is in point contact with the bottom of the jewel bearing 4032. The fixed support part 401 supports, by means of the top cone 4031, the jewel bearing 4032 and the movable support part 401 which are fixedly connected.

In an embodiment of the present invention, the bracket further comprises at least a pair of magnets; for each pair of magnets, the first magnet is fixed to one side, close to the movable support part, on the fixed support part, and the second magnet is fixed to one side, close to the fixed support part, on the movable support part, and the first magnet and the second magnet are stacked in parallel, and the surfaces, which are close each other, of the first magnet and the second magnet are the like magnetic poles. The bracket provided by the embodiment of the present invention will be further described below by taking the bracket which comprises two pairs of magnets as an example.

Figure 5:
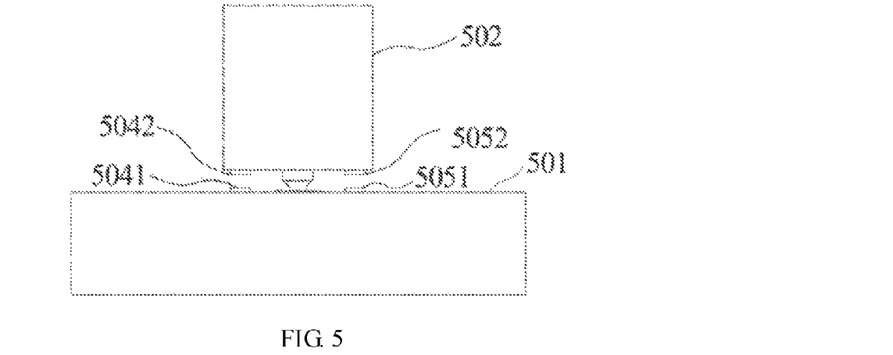
FIG. 5 is a schematic diagram of a bracket comprising magnets as provided by an embodiment of the present invention.

In an embodiment of the present invention, as shown in FIG. 5, the support comprises two pairs of magnets. The first pair of magnets includes a magnet 5041 and a magnet 5042. The second pair of magnets includes a magnet 5051 and a magnet 5052. The magnet 5041 and the magnet 5051 are fixed to the fixed support part 501, and the magnet 5042 and the magnet 5052 are fixed to the movable support part 502. The magnet 5041 and the magnet 5042 in the first pair of magnets are stacked in parallel. The surfaces, which are close to each other, of the magnet 5041 and the magnet 5042 have magnetic poles which have the same polarity, for example, the N pole of the magnet 5041 is directed to the movable support part 502, and the N pole of the magnet 5042 is directed to the fixed support part 501; the magnet 5051 and the magnet 5052 in the second pair of magnets are slacked in parallel; the surfaces, which are close to each other, of the magnet 5051 and the magnet 5052 have magnetic poles which have the same polarity, for example, the S pole of the magnet 5051 is directed to the movable support part 502, and the S pole of the magnet 5052 is directed to the fixed support part 501.

Figure 6:
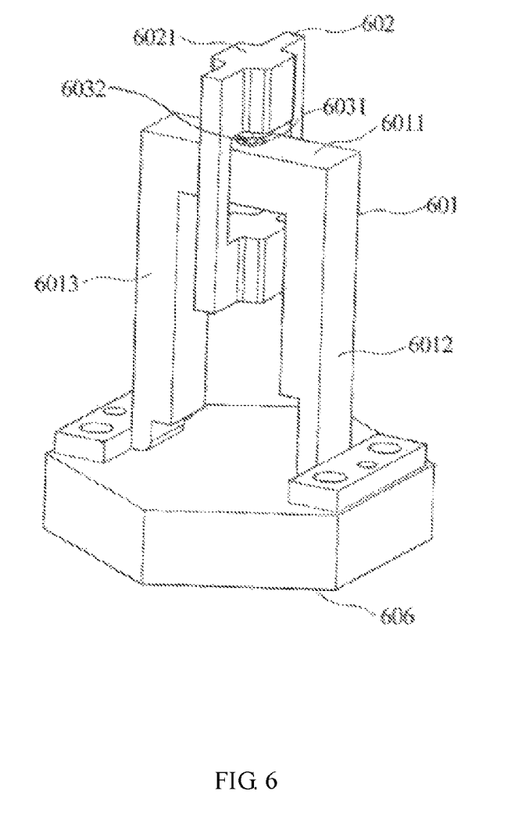
FIG. 6 is a schematic diagram of a bracket comprising a U-shaped fixed support part as provided by an embodiment of the present invention.

In an embodiment of the present invention, as shown in FIG. 6, the fixed support part 601 is of a U-shaped structure. The fixed support part 601 which is of the U-shaped structure comprises a crossbeam 6011, a first longitudinal beam 6012 and a second longitudinal beam 6013, wherein the crossbeam 6011 is fixedly connected between the first longitudinal beam 6012 and the second longitudinal beam 6013, and is fixedly connected to the first fixing connection member 6031. The movable support part 602 is fixedly connected to the second fixing connection member 6032. The first longitudinal beam 6012 and the second longitudinal beam 6013 are fixed, by bolts, to a fixed platform 606 serving as a support surface, and the fixed platform 606 supports the entire bracket.

Figure 7:
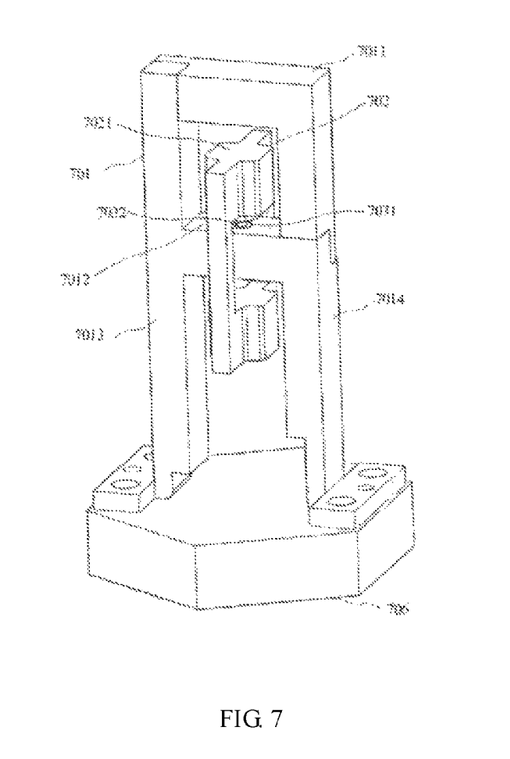
FIG. 7 is a schematic diagram of a bracket comprising a "A"-shaped fixed support part as provided by an embodiment of the present invention.

In an embodiment of the present invention, as shown in FIG. 7, the fixed support part 701 is of a "A"-shaped structure. The fixed support part 701 which is of a "A"-shaped structure comprises a top crossbeam 7011, a middle crossbeam 7012, a first longitudinal beam 7013 and a second longitudinal beam 7014, wherein the two crossbeams are fixedly connected between the two longitudinal beams and a through hole is formed between the two crossbeams. The movable support part 702 passes through a gap between the top crossbeam 7011 and the middle crossbeam 7012. The middle crossbeam 7012 is fixedly connected to the first fixing connection member 7031. The first fixing connection member is matched with the second fixing connection member 7032 fixed on the movable support part 702. The middle crossbeam 7012 supports the movable support part 702. The first longitudinal beam 7013 and the second longitudinal beam 7014 are fixed, by bolts, to the fixed platform 706 which serves as the support surface. The fixed platform 706 supports the entire bracket.

In the embodiment of the present invention, the top crossbeam 7012 is detachably connected to the first longitudinal beam 7013 and the second longitudinal beam 7014 to facilitate the mounting and detachment of the movable support part 702.

In an embodiment of the present invention, as shown in FIGS. 6 and 7, wherein the movable support part is of a regular quadrangular frame structure having a through hole in the middle. The first crossbeam on the movable support part is fixedly connected to the first fixing connection member. A support crossbeam fixed on the connection part passes through the through hole in the movable support part which is of the frame structure, and the second fixing connection member fixed on the support crossbeam is matched with the first fixing connection member. The second crossbeam on the movable support part, which is opposite to the first crossbeam, is fixedly connected to the external supported object. As shown in FIG. 6, the crossbeam 6011 passes through the through hole in the middle of the movable support part 602, and is connected to the first crossbeam 6021 on the movable support part 602 by means of the first fixing connection member 6031 and the second fixing connection member 6032. As shown in FIG. 7, the middle crossbeam 7012 passes through the through hole in the middle of the movable support part 702, and is connected to the first crossbeam 7012 on the movable support part 702 by means of the first fixing connection member 6031 and the second fixing connection member 6032.

Figure 8:
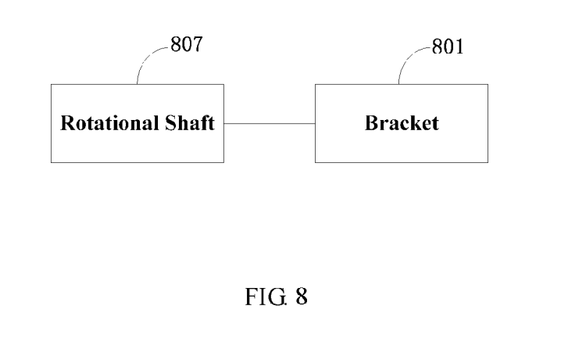
FIG. 8 is a schematic diagram of a thrombelastography device provided by an embodiment of the present invention.

As shown in FIG. 8, an embodiment of the present invention provides a thrombelastography device, comprising a rotational shaft 807 and any bracket 801 provided by the embodiments of the present invention, wherein the rotational shaft 807 which serves as the supported object is fixedly connected to the movable support part in the bracket 801; and the rotational shaft 807 can rotate the movable support part to rotate under the driving force of the measured blood.

Figure 9:
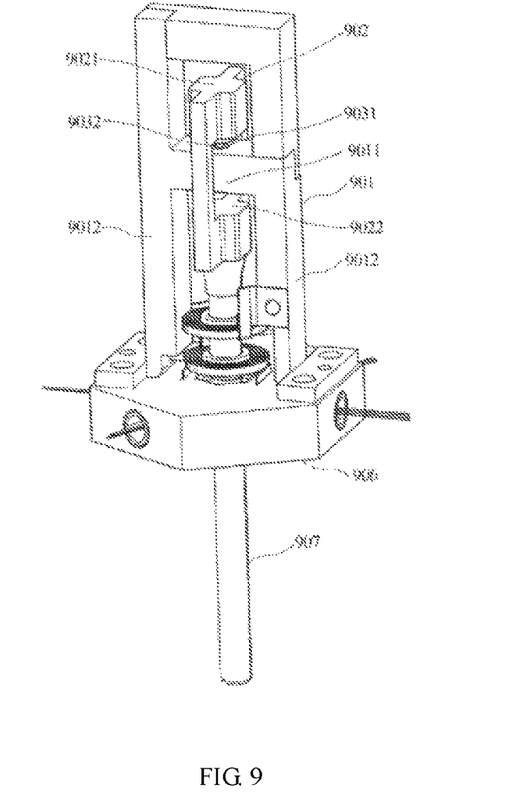
FIG. 9 is a schematic diagram of a thrombelastography device provided by another embodiment of the present invention.

In an embodiment of the present invention, as shown in FIG. 9, a thrombelastography device comprises a rotational shaft 907, a fixed platform 906 and the bracket as shown in FIG. 7, wherein a first fixing connection member 9031 in the bracket is fixed to a middle crossbeam 9011 of a fixed support part 901, a second fixing connection member 9032 is fixed to a crossbeam 9021 on the upper part of a movable support part 902, and the first fixing connection member 9031 is matched with the second fixing connection member 9032, such that the fixed support part 901 is connected to the movable support part 902 in point contact fashion;

a crossbeam 9022 on the lower part of the movable support part 902 is fixedly connected to the rotational shaft 907; and two longitudinal beams 9012 of the fixed support part 901 are fixed to the fixed platform 906 by means of bolts, and the fixed platform 906 supports the entire bracket and the rotational shaft 907.

In an embodiment of the present invention, the first fixing connection member 9031 is a jewel bearing, and the second fixing connection member 32 is a top cone, wherein the tip of the top cone is located in a tapered groove of the jewel bearing, the tip of the top cone is in point contact with the bottom of the tapered groove, and the fixed support part 901 supports the movable support part 902 and the rotational shaft 907 by means of the point contact. It will be understood that the first fixing connection member may also be made of any other appropriately rigid materials, such as glass, alloys, metal, or the like.

Figure 10:
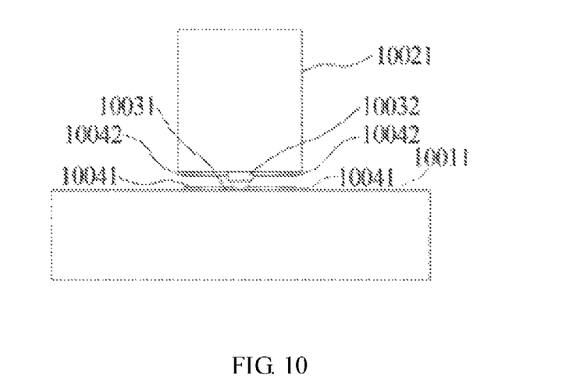
FIG. 10 is a schematic diagram of a thrombelastography device comprising an annular magnet as provided by an embodiment of the present invention.

In an embodiment of the present invention, the thrombelastography device as shown in FIG. 9 may further comprise a pair of annular magnets. As shown in FIG. 10, the first annular magnet 10041 in the pair of annular magnets is fixed on a middle crossbeam 10011 of the fixed support part, and the axis of the first annular magnet 10041 is overlapped with the axis of the first fixing connection member 10031 (a jewel bearing); the second annular magnet 10042 in the pair of annular magnets is fixed on an upper crossbeam 10021 of the movable support part, and the axis of the second annular magnet 10042 is overlapped with the axis of the second fixing connection member 10032 (a top cone); the magnetic pole of the first annular magnet 10041, which is directed to the upper crossbeam 10021 of the movable support part and the magnetic pole of the second annular magnet 10042, which is directed to the middle crossbeam 10011 of the fixed support part are like magnetic poles. For example, under a positional state shown in FIG. 10, the upward direction of the first annular magnet 10041 is the N pole, and the downward direction of the second annular magnet 10042 is the N pole.

Figure 11:
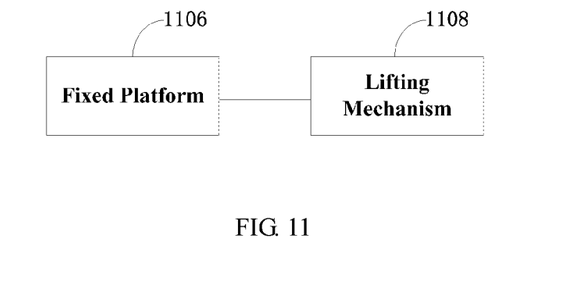
FIG. 11 is a schematic diagram of a thrombelastography device comprising a lifting mechanism as provided by an embodiment of the present invention.

In an embodiment of the present invention, as shown in FIG. 11, the thrombelastography device may further comprise a lifting mechanism 1108 which is connected to the fixed platform 1106. The fixed platform 1106 may ascend or descend by means of the lifting mechanism 1108, thereby driving the bracket and the rotational shaft to ascend or descend and facilitating putting the rotational shaft in measured blood or taking the rotational shaft out of the measured blood.

Figure 12:
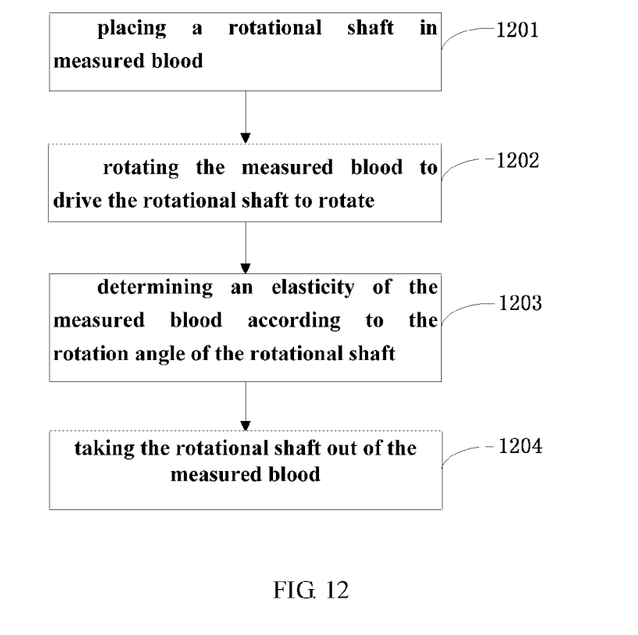
FIG. 12 is a flowchart of a use method for a thrombelastography device as provided by an embodiment of the present invention.

In order to illustrate the structure of the thrombelastography device provided by the embodiment of the present invention more clearly, a use method for the thrombelastography device will be described below in conjunction with the thrombelastography device shown in FIG. 9. As shown in FIG. 12, an embodiment of the present invention provides a use method for a thrombelastography device, comprising the following steps 1201-1204.

Step 1201: placing a rotational shaft in measured blood.

In an embodiment of the present invention, when the blood is measured by the thrombelastography device shown in FIG. 9, the measured blood is placed in a blood container. The blood container is placed below the fixed platform 906. The fixed platform 906 is driven by the lifting mechanism to descend. The rotational shaft 907 extends into the blood container under the driving of the fixed platform 906, such that the rotational shaft 907 is immersed into the measured blood by a specified length.

Step 1202: rotating the measured blood to drive the rotational shaft to rotate.

In an embodiment of the present invention, after the lower end of the rotational shaft 907 is immersed in the measured blood by a specified length, the blood container is rotated at a certain speed by a rotating device, and the blood container rotates to drive the measured blood to rotate. Since the measured blood has a certain viscosity, the measured blood rotates on the rotational shaft 907 to generate a rotational moment, and the rotational shaft 907 rotates under the action of the rotating moment. The larger the viscosity of the measured blood, the larger the rotation angle of the rotational shaft 907.

In an embodiment of the present invention, since the rotational shaft 907 is fixedly connected to the movable support part 902, when the rotational shaft 907 rotates, the movable support part 902 rotates at the same angle as the rotational shaft 907 around the contact point between the jewel bearing 9031 and the top cone 9032. The fixed support part 901 supports the rotational shaft 907 and the movable support part 902 by means of the jewel bearing 9031 and the top cone 9032. Since the jewel bearing 9031 and the top cone 9032 are in single-point contact, the frictional force generated when the jewel bearing 9031 and the top cone 9032 rotate relative to each other is relatively small, thereby reducing the rotational resistance of the bracket to the rotational shaft 907 when the rotational shaft 907 rotates.

step 1203: determining an elasticity of the measured blood according to the rotation angle of the rotational shaft.

In an embodiment of the present invention, the rotation angle of the rotational shaft 907 is sensed through various sensors, a thrombelastogram is formed according to the rotation angle of the rotational shaft, and an index parameter reflecting the elasticity of the measured blood is obtained according to the thrombelastogram; or the rotation angle of the rotational shaft 907 is directly converted to an index parameter that reflects the elasticity of the measured blood.

Step 1204: taking the rotational shaft out of the measured blood.

In an embodiment of the present invention, after the elasticity of the measured blood is acquired, the fixed platform 906 ascends by means of the lifting mechanism to drive the fixed support part 901 fixedly connected thereto to ascend. Since the fixed support part 901 supports the movable support part 902 by means of the jewel bearing 9031 and the top cone 9032, the fixed support part 901 ascends to drive the movable support part 902 to ascend. In addition, since the movable support part 902 is fixedly connected to the rotational shaft 907, the movable support part 902 ascends to drive the rotational shaft 907 to ascend, such that the rotational shaft 907 is taken out of the blood container to complete the measurement of the measured blood.

Figure 13:
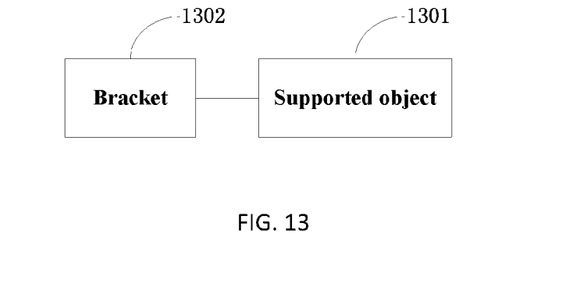
FIG. 13 is a schematic diagram of a support system provided by an embodiment of the present invention.

As shown in FIG. 13, an embodiment of the present invention further provides a support system, which comprises a supported object 1301 and any bracket 1301 provided by the embodiments of the present invention, wherein the supported object 1301 is fixedly connected to the movable support part in the bracket 1302, and the supported object 1301 can drive, under an external driving force, the movable support part to rotate.

An embodiment of the present invention provides a use method for a support system, which comprises the following steps:

Step A: accepting, by the supported object, an external driving force; and

Step B: driving, by the supported object under the external driving force, the movable support part to rotate.

In the Step B, the supported object is fixedly connected to the movable support part, and the fixed support part is connected to the movable support part in point contact fashion. The supported object drives, under the external driving force, the movable support part to rotate around the contact point of the point contact. Since the fixed support part supports the movable support part and the supported object only by one contact point, the frictional force generated when the movable support portion and the fixed support portion rotate relative to each other is relatively small, thereby reducing the rotational resistance encountered when the supported object rotates.

In an embodiment of the present invention, when the rotational shaft is used as one of the supported objects, the support system is the thrombelastography device provided by the above embodiments. When a rotational component of the rotational shaft is used as the supported object, the support system may be applied to other machines and equipment.

It should be noted that, in the embodiment of the present invention, any type of bracket can be used in the thrombelastography device, and can of course be used in other devices to complete the supporting function thereof and reduce the rotational resistance encountered when the supported object, such as the thrombelastography device rotates.

Various embodiments provided by the present invention have the following beneficial effects:

1. in the embodiment of the present invention, the fixed support part supports the movable support part and the supported object by means of the connection part, and the first fixing connection member and the second fixing connection member in the connection part are connected together in point contact fashion, such that the supported object which is stress can drive the movable support part to rotate around the contact point between the first fixing connection member and the second fixed connection member. Since the first fixing connection member and the second fixing connection member are connected together in point contact fashion, when the movable support part rotates relative to the fixed support part, only one contact point generates a frictional force to impede the rotation of the movable support part. Therefore, the frictional force generated on the bracket may be very small, and further the rotational resistance encountered when the supported object rotates is reduced.

2. In the embodiment of the present invention, two fixing connection members included in the connection part may be the jewel bearing and the top cone. The tip of the top cone is located in the tapered groove of the jewel bearing, and the tip of the top cone is in point contact with the bottom of the tapered groove. When the jewel bearing rotates relative to the top cone, a less frictional force is generated, such that the rotational resistance from the bracket when the supported object rotates can be reduced. The sensitivity and the measurement accuracy of the thrombelastography device may be improved when the bracket is applied to the thrombelastography device.

3. in the embodiment of the present invention, the jewel bearing may be fixed either on the fixed support part or on the movable support part, and correspondingly the top cone may be fixed on the movable support part or the fixed support part, which may be selected flexibly according to structures and functions, thereby improving the applicability of the bracket.

4. In the embodiment of the present invention, the bracket may comprise at least a pair of magnets, wherein one magnet in each pair of magnets is fixed to the fixed support part, and the other magnet thereof is fixed to the movable support part. The pair of magnets is stacked in parallel, and like magnetic poles are opposite. In this way, according to the principle that like poles repel each other, the magnet on the fixed support part applies an upward magnetic force to the magnet on the movable support part. The magnetic force can reduce the pressure of the point contact between the first fixing connection member and the second fixing connection member, and further reduce the frictional force generated by the point contact, thereby further reducing the rotational resistance encountered when the supported object rotates.

5. In the embodiment of the present invention, the fixed support part may be of U-shaped structure or a "A"-shaped structure, which may be selected flexibly as required, thereby improving the applicability of the bracket. When the "A"-shaped structure is applied to the thrombelastography device, the top crossbeam may play a certain role of protecting the movable support part, thereby avoiding accidentally contacting the movable support part during the measurement process, and further improving the reliability of measurement results of the thrombelastography device.

It can be appreciated that, while the relationship terms "first", "second" and so on may be used herein to distinguish one entity or operation from another, it does not require or imply such an actual relation or sequence between these entities or operations. Further, the terms "include", "comprise" or any variation thereof are intended to cover an nonexclusive containing, such that a process, a method, an item or a device containing a series of elements not only includes these elements, but also includes other elements that are not set forth specifically, or also includes an inherent element of such a process, method, item or device. Without further limitation, an element defined by a phrase "include a" does not mean that other elements are excluded from the process, method, item or device.

Aspects of the Invention

The various aspects numbered below further provide the disclosure of the present invention.

1. A bracket, comprising: a fixed support part, a movable support part, and a connection part; wherein the connection part comprises a first fixing connection member and a second fixing connection member;

the first fixing connection member is fixedly connected to the fixed support part;

the second fixing connection member is fixedly connected to the movable support part;

the first fixing connection member is connected to the second fixing connection member in point contact fashion, such that the first fixing connection member and the second fixing connection member can rotate relative to each other;

the movable support part is fixedly connected to a supported object; and when driven by the supported object, the movable support part rotates relative to the fixed support part by means of the point contact between the first fixing connection member and the second fixing connection member.

2. The bracket according to aspect 1, wherein the first fixing connection member is a bearing ; and the second fixing connection member is of a tapered structure;

or the first fixing connection member is of a tapered structure, and the second fixing connection member is a bearing; wherein the bearing is provided with a tapered groove, and the tip of the tapered structure is located in the tapered groove, such that the tapered structure is connected to the bearing in point contact fashion.

3. The bracket according to aspect 1, wherein the first fixing connection member comprises a jewel bearing, and the second fixing connection member comprises a top cone;

or the first fixing connection member comprises a top cone, and the second fixing connection member comprises a jewel bearing; wherein the jewel bearing is provided with a tapered groove; the top cone may be of a tapered structure; the tip of the top cone is located in the tapered groove on the jewel bearing; and the top cone is connected to the jewel bearing in point contact fashion.

4. The bracket according to aspect 1, further comprising at least a pair of magnets; wherein for each pair of magnets, the first magnet is fixed to one side, close to the movable support part, on the fixed support part, and the second magnet is fixed to one side, close to the fixed support part, on the movable support part; and the first magnet and the second magnet are stacked in parallel, and two surfaces that are close each other have like magnetic poles.

5. The bracket according to aspect 1, wherein the fixed support part is of a U-shaped structure and comprises two longitudinal beams and a crossbeam fixedly connected between the two longitudinal beams; and the crossbeam which is of the U-shaped structure is fixedly connected to the first fixing connection member.

6. The bracket according to aspect 5, wherein the two longitudinal beams are fixed to a support surface to support the crossbeam, and support the movable support part by means of the connection part.

7. The bracket according to aspect 1, wherein the fixed support part is of a "A"-shaped structure, and comprises two longitudinal beams and two crossbeams fixedly connected between the two longitudinal beams, wherein a through hole is formed between the two crossbeams; and the movable support part passes through the through hole and is connected to the crossbeam in the middle of the "A"-shaped structure by means of the connection part.

8. The bracket according to aspect 7, wherein the two longitudinal beams are fixed to a support surface to support the two crossbeams, and support the movable support part by means of the connection part.

9. The bracket according to any one of aspects 1 to 8, wherein the movable supporting part is of a regular quadrangular frame structure having a through hole in the middle, and comprises a first crossbeam, a second crossbeam, a first longitudinal beam and a second longitudinal beam, wherein the first crossbeam is fixedly connected to the second fixing connection member;

the fixed support part passes through the through hole in the movable support part, and is connected to the first crossbeam of the movable support part by means of the connection part; and the second crossbeam of the movable support part can be fixedly connected to the supported object.

10. A thrombelastography device, comprising a rotational shaft and the bracket according to any of aspects 1 to 6, wherein the rotational shaft which serves as the supported object is fixedly connected to the movable support part in the bracket: and the rotational shaft drives the movable support part to rotate under the driving force of the measured blood.

11. The thrombelastography device according to aspect 10, wherein when the fixed support part is of a U-shaped structure or a "A"-shaped structure, the thrombelastography device further comprises a fixed platform, wherein the fixed platform is fixedly connected to the two longitudinal beams of the fixed support part.

12. The thrombelastography device according to aspect 11, further comprising a lifting mechanism, wherein the lifting mechanism is connected to the fixed platform and drives the fixed platform to ascend or descend.

13. A support system, comprising a supported object and the bracket according to any one of aspects 1 to 9, wherein the supported object is fixedly connected to the movable support part in the bracket, and can drive, under an external driving force, the movable support part to rotate.

14. A use method for a thrombelastography device, wherein the thrombelastography device is the thrombelastography device according to any one of aspects 10 to 12, and the method comprises:

placing a rotational shaft in measured blood;

rotating the measured blood to drive the rotational shaft to rotate, wherein during rotation, the first fixing connection member is in point contact with the second fixing connection member; and determining an elasticity of the measured blood according to the rotation angle of the rotational shaft.

15. A use method for the support system, wherein the support system is the support system according to aspect 13, and the method comprises:

accepting, by the supported object, an external driving force; and driving, by the supported object under the external driving force, the movable support part to rotate, wherein during rotation, the first fixing connection member is in point contact with the second fixing connection member.

It should be eventually noted that the above contents are only preferred embodiments of the present invention, and used only for describing the technical solutions of the present invention, rather than limiting the protection scope of the present invention. Any modifications, equivalent substitutions, improvements, etc. made within the spirit and principle of the present invention should be included within the protection scope of the present invention.

What is claimed is:

1. A bracket, comprising: a fixed support part, a movable support part, and a connection part; wherein
the connection part comprises a first fixing connection member and a second fixing connection member;
the first fixing connection member is fixedly connected to the fixed support part;
the second fixing connection member is fixedly connected to the movable support part;
the first fixing connection member is connected to the second fixing connection member downward point contact fashion of the second fixing connection member on the first fixing connection member, such that the first fixing connection member and the second fixing connection member can rotate relative to each other;
the movable support part is fixedly connected to a supported object; and
when driven by the supported object, the movable support part rotates relative to the fixed support part by means of the downward point contact of the second fixing connection member on the first fixing connection member, the downward point contact being the only point contact between the fixed support part and the movable support part.

2. The bracket according to claim 1, wherein
the first fixing connection member is of a tapered structure, and the second fixing connection member is a bearing; wherein
the bearing is provided with a tapered groove, and the tip of the tapered structure is located in the tapered groove, such that the tapered structure is connected to the bearing in point contact fashion.

3. The bracket according to claim 1, wherein
the first fixing connection member comprises a top cone, and the second fixing connection member comprises a jewel bearing; wherein
the jewel bearing is provided with a tapered groove; the top cone is of a tapered structure; the tip of the top cone is located in the tapered groove on the jewel bearing; and the top cone is connected to the jewel bearing in point contact fashion.

4. The bracket according to claim 1, further comprising at least a pair of magnets; wherein
for each pair of magnets, the first magnet is fixed to one side, close to the movable support part, on the fixed support part, and the second magnet is fixed to one side, close to the fixed support part, on the movable support part; and
the first magnet and the second magnet are stacked in parallel, and two surfaces that are close each other have like magnetic poles.

5. The bracket according to claim 1, wherein
comprises two longitudinal beams and a crossbeam fixedly connected between the two longitudinal beams; and
the crossbeam is fixedly connected to the first fixing connection member.

6. The bracket according to claim 5, wherein the two longitudinal beams are fixed to a support surface to support the crossbeam, and support the movable support part by means of the connection part.

7. The bracket according to claim 1, wherein
the fixed support part comprises two longitudinal beams and two crossbeams fixedly connected between the two longitudinal beams, wherein a through hole is formed between the two crossbeams; and the movable support part passes through the through hole and is connected to the crossbeam by means of the connection part.

8. The bracket according to claim 7, wherein the two longitudinal beams are fixed to a support surface to support the two crossbeams, and support the movable support part by means of the connection part.

9. A support system, comprising the supported object and the bracket according to claim 1, wherein
the supported object can drive, under an external driving force, the movable support part to rotate.

10. A bracket comprising: a fixed support part, a movable support part, and a connection part; wherein
the connection part comprises a first fixing connection member and a second fixing connection member;
the first fixing connection member is fixedly connected to the fixed support part;
the second fixing connection member is fixedly connected to the movable support part;
the first fixing connection member is connected to the second fixing connection member in a downward point contact fashion of the second fixing connection member on the first fixing connection member, such that the first fixing connection member and the second fixing connection member can rotate relative to each other;
the movable support part is fixedly connected to a supported object; and
when driven by the supported object, the movable support part rotates relative to the fixed support part by means of the downward point contact of the second fixing connection member on the first fixing connection member, the downward point contact being the only point contact between the fixed support part and the movable support part,
the movable support part is of a regular quadrangular frame structure having a through hole in the middle, and comprises a first crossbeam, a second crossbeam, a first longitudinal beam and a second longitudinal beam, wherein the first crossbeam is fixedly connected to the second fixing connection member;
the fixed support part passes through the through hole in the movable support part, and is connected to the first crossbeam of the movable support part by means of the connection part; and
the second crossbeam of the movable support part is fixedly connected to the supported object.

11. A thrombelastography device, comprising a rotational shaft and a bracket, wherein the bracket comprises a fixed support part, a movable support part, and a connection part, wherein
the connection part comprises a first fixing connection member and a second fixing connection member;
the first fixing connection member is fixedly connected to the fixed support part;
the second fixing connection member is fixedly connected to the movable support part;
the first fixing connection member is connected to the second fixing connection member in a downward point contact fashion of the second fixing connection member on the first fixing connection member, such that the first fixing connection member and the second fixing connection member can rotate relative to each other;
the movable support part is fixedly connected to a supported object; and
when driven by the supported object, the movable support part rotates relative to the fixed support part by means of the downward point contact of the second fixing connection member on the first fixing connection member, the downward point contact being the only point contact between the fixed support part and the movable support part,
wherein
the rotational shaft which serves as the supported object is fixedly connected to the movable support part in the bracket;
the rotational shaft can drive the movable support part to rotate under the driving force of the measured blood;
a fixed platform; and
two longitudinal beams forming part the fixed support part, wherein the fixed platform is fixedly connected to the two longitudinal beams.

12. The thrombelastography device according to claim 11, further comprising a lifting mechanism, wherein
the lifting mechanism is connected to the fixed platform and drives the fixed platform to ascend or descend.

* * * * *

UNITED STATES PATENT AND TRADEMARK OFFICE
CERTIFICATE OF CORRECTION

| | | |
|---|---|---|
| PATENT NO. | : 12,169,195 B2 | Page 1 of 1 |
| APPLICATION NO. | : 18/380967 | |
| DATED | : December 17, 2024 | |
| INVENTOR(S) | : Jian Xiao et al. | |

It is certified that error appears in the above-identified patent and that said Letters Patent is hereby corrected as shown below:

In the Claims

At Column 13, Claim number 5, Line numbers 53 and 54, please replace "wherein comprises" with --further comprising--

At Column 15, Claim number 11, Line number 12, please insert --of-- between "part" and "the"

Signed and Sealed this
Eleventh Day of February, 2025

Coke Morgan Stewart
*Acting Director of the United States Patent and Trademark Office*